United States Patent [19]

Kesslin et al.

[11] 4,322,548

[45] Mar. 30, 1982

[54] RESOLUTION OF RACEMIC MANDELIC ACID

[75] Inventors: George Kesslin, Teaneck, N.J.; Kenneth W. Kelly, New City, N.Y.

[73] Assignee: Kay Fries, Inc., Stony Point, N.Y.

[21] Appl. No.: 121,331

[22] Filed: Feb. 13, 1980

[51] Int. Cl.³ .............................................. C07B 19/00
[52] U.S. Cl. ............................... 562/401; 260/501.17; 560/43
[58] Field of Search .................. 562/401; 260/501.17; 560/43

[56] References Cited

U.S. PATENT DOCUMENTS 2,820,827  1/1958  Ruschig et al. ...................... 562/401
3,887,606  6/1975  Phillipps et al. ..................... 562/401

FOREIGN PATENT DOCUMENTS 6187  1/1980  European Pat. Off. ............ 562/401
2733425  1/1979  Fed. Rep. of Germany .

OTHER PUBLICATIONS

McKenzie, *J. Chem. Soc.*, 75, p. 966, (1899).
Ingersoll et al., *J. Amer. Chem Soc.*, 55, p. 411, (1933).
Roger, *J. Chem. Soc.*, p. 1544, (1935).
Blaschke, *Chem. Ber.*, 107, p. 237, (1974).

*Primary Examiner*—Natalie Trousof
*Assistant Examiner*—Vera C. Clarke
*Attorney, Agent, or Firm*—Sprung, Felfe, Horn, Lynch & Kramer

[57] ABSTRACT

Process for the optical resolution of racemic mandelic acid which process comprises contacting said racemic mandelic acid with a phenylglycine ester or a phenylglycine ester hydrochloride in a reaction medium, and recovering the D(−)-mandelic acid and L(+)-mandelic acid form; certain D(−) and L(+)-phenylglycine esters and hydrochlorides are provided as novel resolution agents.

26 Claims, No Drawings

RESOLUTION OF RACEMIC MANDELIC ACID

This invention relates to a process for the resolution of racemic mandelic acid, more specifically for the optical resolution of racemic mandelic acid using certain phenylglycine compounds. In additional aspect, the invention provides novel phenylglycine compounds useful in such resolution.

Optically active mandelic acid derivatives are useful in the separation of racemic amines into optically active enantiomers. In addition, D(−)-mandelic acid is an important intermediate in the preparation of semi-synthetic cephalosporins.

Processes for the separation of DL-mandelic acid into its optical antipodes are known. Thus, S. H. Wilen teaches, in "Tables of Resolving Agents and Optical Resolution" (1972), Notre Dame, Ind.), cinchonine, cinchonidine, phenylethylamine, ephedrine, strychnine and morphine as separation reagents for DL-mandelic acid. These optically active amines form diastereomeric salts with DL-mandelic acid, rendering them useful for such separation.

In the separation of DL-mandelic acid with cinchonine, using equimolar amounts and an aqueous solvent medium, the crystallization of the diastereomeric salt must be initiated by high temperature inoculation. To improve the optical purity of the product involved, recrystallizations are necessary and this leads to yields of perhaps 80% of the diastereomer which yields (+)-mandelic acid after cleavage (see A. McKenzie, J. Chem. Soc. 75 (1899) 966).

When resolving DL-mandelic acid with (+)-phenylethylamine in aqueous solution, again several recrystallizations are required to obtain adequate optical purity and yields of only 86% are achievable; see A. W. Ingersoll et al., J.Am.Chem.Soc. 55 (1933) at 411. When using ephedrine in ethanol solution, yields of, at most, 85% of the diastereomer can be obtained, but only after several recrystallizations and working up of relatively large amounts of solvent; see R. Roger, J.Chem.Soc. (1935) at page 1544.

The use of phenylethylamine and ephedrine is, however, limited due to cost factors and in addition, these materials have relatively high molecular weights so that use of relatively large quantities is required. Similar separations using morphine, strychnine and cinchonidine also suffer from these disadvantages and of course the use of strychnine is difficult due to its extreme toxicity.

More recent publications disclose resolution of DL-mandelic acid on optically active polymers by chromotography or ion exchange effects (G. Blaschke, Chem.Ber. 107, (1974) 237). The carrier material chosen is treated with optically active amines in these processes. However, these techniques have been found to result in incomplete reactions and relatively low yields and have not found commercial favor.

Still more recently, German patent publication No. 27 33 425 discloses a chemical separation of racemic mandelic acid by reacting same with D(−)-2-aminobutanol and recrystallizing the resulting D-(−)-2-amino-1-butanol D-(−)-mandelate from water an aliphatic alcohol, or a ketone, followed by recovery of D-(−)-mandelic acid from the salt and L-(+)-mandelic acid from the mother liquor. However, the 2-amino-1-butanol used is costly and not available in commercial quantities.

Accordingly, there has been a need for the optical reslution of racemic mandelic acid using a relatively cheap and available separation agent which produces high yields and high purity of the desired optical components and is characterized by low toxicity.

The present invention provides such a process and resolution agents which substantially overcome the disadvantages inherent in prior art techniques.

Essentially, the present invention provides a process for the optical resolution of racemic mandelic acid using an alkyl ester of dextro- or levorotatory-phenylglycine, e.g., the butyl ester of D(−) or L(+) phenylglycine, or their hydrochloride salts. The usable esters, which include the methyl, isopropyl and n-decyl esters in addition to the butyl esters, are readily synthesized from commercially available D(−) or L(+) phenylglycine and do not have the undesirable properties of the materials previously employed.

In additional aspect, the invention provides, as novel compositions of the matter, certain of the resolution agents used herein. Thus, the invention provides D(−) phenylglycine esters containing more than 4 carbon atoms in the alkyl group as well as their corresponding hydrochorides, e.g., the pentyl ester, the decyl ester and stearyl ester of D(−) phenylglycine and their hydrochlorides). In addition, there are provided the ester hydrochlorides of L(+) phenylglycine, e.g., L(+)phenylglycine alkyl ester hydrochlorides wherein the alkyl ester moiety contains 4 to 18 carbon atoms, e.g., the isobutyl ester hydrochloride, the tert.-butyl ester hydrochloride, the pentyl ester hydrochloride and the stearyl ester hydrochloride of L(+)phenyglycine.

To effect the optical resolution of racemic mandelic acid, the mandelic acid is contacted with the phenylglycine ester (or hydrochloride thereof) and preferably 0.5 to 1 mole of phenylglycine ester is used per mole of DL-mandelic acid. In the case of the ester hydrochloride salts, the preferred ratio is 0.5 to 1.2 moles of phenylglycine ester hydrochloride per mole of racemic mandelic acid. In general, it will be found most economical to use the lower mole proportion of the phenylglycine ester (hydrochloride), i.e., about one-half mole per mole of racemic mandelic acid to be resolved. After mixing the phenylglycine ester (hydrochloride) and the racemic mandelic acid, the resulting mixture is filtered and, in the case of use of the hydrochloride, neutralized with an alkali, e.g., an alkali hydroxide. For instance, 0.7 to 1.0 moles of sodium hydroxide can be used per mole of hydrochloride initially employed and preferably about 0.75 moles of sodium hydroxide are employed per mole of starting phenyglycine hydrochloride.

The resolution medium can be water or alcohol or mixtures thereof and suitable alcohols are methanol, ethanol, isopropanol, butanol and the like. In general, water is preferred as being the most convenient and economical resolution medium. The temperature ranges at which resolution is carried out can range from 0° C. to 35° C., with ambient temperatures, i.e. 20° to 30° C., being preferred.

The method of isolating the dextrorotatory or levorotatory optical antipodes of mandelic acid is not narrowly critical. For instance, in the case of an aqueous resolution medium, they may be extracted with water immiscible solvents, such as methylisobutyl ketone or ether. However, isolation can also be effected by other conventional techniques for isolating a water-soluble organic acid from an aqueous medium.

In a preferred embodiment of the invention, the D(—)phenylglycine ester used for resolution can be recovered by neutralizing the aqueous layer remaining after extraction of the D(—)mandelic acid, e.g., with methylisobutyl ketone, and separating the water insoluble D(—)phenylglycine ester. Any suitable solvent, such as methylene chloride, toluene, methylisobutyl ketone, ether and the like can be used to extract and separate the phenylglycine ester from the neutral aqueous medium. Recovery of D(—)phenylglycine ester is illustrated in Examples 1 and 5 infra. The L(+)phenylglycine ester can similarly be recovered from the aqueous layer remaining after extraction of D(—)mandelic acid. Recovery of L(+)phenylglycine ester is illustrated in Example 11 infra.

The following examples are illustrative.

EXAMPLE 1

Resolution of racemic mandelic acid with D(—)phenylglycine butyl hydrochloride

A mixture of 60.9 grams of D(—)-phenylglycine butyl ester hydrochloride (0.25 mole) 76 grams racemic mandelic acid (0.50 mole) and 1000 ml $H_2O$ was stirred at 25° C. until solution occurred. An insoluble, tan precipitate was filtered off, leaving a lemon-yellow filtrate. To the filtrate was added 7.44 grams NaOH dissolved in 65 ml water, over a 20 minute period at 22° C. A voluminous precipitate of white solids occurred during the latter stages of NaOH addition. 750 ml more water was added to assist stirring, but stirring was still difficult. The slurry was filtered, the filter cake sucked dry and washed with 50 ml water, resulting in white solids having an air-dry weight of 79.2 grams, consisting of optically impure D(—) phenylglycine butyl ester L(+) mandelic acid.

The filtrate (1500 ml) was concentrated at 40° C. and 29″ of vacuum to approximately 600 ml total volume, cooled to 25° C. and an additional quantity of optically impure D(—) phenylglycine butyl ester L(+) mandelic acid filtered off; air-dry weight=19.1 grams; (total salt weight - 98.3 grams; theory=89.8 grams). The filtrate (590 ml) was acidified with 12.8 grams conc. $H_2SO_4$ and extracted three times with 200 ml methylisobutyl ketone.

The combined methylisobutyl ketone layers were evaporated to dryness at 60° C. and 20″ of vacuum, to yield 13.3 grams D(—)-mandelic acid specific rotation, using sodium lamp D-line wavelength, of —73° (water) corresponding to 35% of theory. Two recrystallizations from water yielded D(—)-mandelic acid, specific rotation, using sodium lamp D-line wavelength, of —154.2° (water). This substantially matched the value reported by Heilbron of —158° (water). The product was over 99% pure by acid-base titration; and identical in NMR and IR spectra with authentic commercial D(—)-mandelic acid.

EXAMPLES 2-4

Resolution of Racemic Mandelic Acid Using Other Resolving Agents

Using the method of Example 1, racemic mandelic acid was resolved in separate experiments with D(—) phenylglycine methyl ester HCl, D(—) phenylglycine isopropylester HCl, and D(—) phenylglycine decyl ester DCl. The following table gives the results of these experiments (compared with phenylglycine butyl ester):

| Example No. | Resolving Agent | Specific rotation using sodium lamp D-line wavelength | Yield | Type of precipitate upon NaOH addn. |
|---|---|---|---|---|
| 1 | D(—) phenylglycine methyl ester hydrochloride | —3.6° | 133% | oil |
| 2 | D(—) phenylglycine isopropylester hydrochloride | —39.5° | 42.8% | oil, then solid |
| 3 | D(—) phenylglycine butyl ester hydrochloride | —73.1° | 35% | solid |
| 4 | D(—) phenylglycine decyl ester hydrochloride | —28.1° | 32% | solid then oily solid |

EXAMPLE 5

Resolution of Racemic Mandelic Acid with D(—) phenylglycine butyl ester (free)

Dissolved 2 moles of racemic mandelic acid in 1500 ml. water and slowly added 1 mole of D(—) phenylglycine butyl ester. Waxy solids form which become discrete solids, with stirring. The final slurry is quite thick. Filtered slurry and washed cake with 100 ml. water. Air-dry weight of filtered solids=370 grams of optically impure D(—) phenylglycine butyl ester L(+) mandelic acid (Theory=358 grams D(—) phenylglycine butyl ester L(+) mandelic acid).

The filtrate was acidified with 1 mole conc. $H_2SO_4$ and extracted with 2×2000 ml methyl isobutyl ketone. The combined methyl isobutyl ketone layers were evaporated to dryness at 60° C. and 29″ of vacuum, to yield 35 grams D(—) mandelic acid, specific rotation, using sodium lamp D-line wavelength=—21.4° C. (water). Repeated recrystallization from water yielded optically pure D(—) mandelic acid.

EXAMPLE 6

Synthesis of D(—) phenylglycine butyl ester hydrochloride

To 1020 ml n-butanol was added 231 grams D(—) phenylglycine acid chloride hydrochloride (1.12 m) over approximately 20 minutes, with reaction temperature allowed to rise from 25° C. to 40°-50° C., using warming as necessary to maintain temperature at 40°-50° C. for approximately 1 hour. Complete solution occurs, and HCl evolves.

The reaction mixture was evaporated at 55° C. and 29″ of vacuum to a soggy solid. Removed solids from reaction vessel and air-dried. Weight of air-dried, white solids=268.7 grams D(—) phenylglycine butyl ester hydrochloride (Theory=272.7 grams); melting point 147°-149° C.; specific rotation, using sodium lamp D-line wavelength=—91.3° (1 N HCl).

EXAMPLE 7

Synthesis of D(—) phenylglycine butyl ester

To 6.3 gram $NaHCO_3$ (0.075 mole) dissolved in 75 ml water was added a mixture 50 ml of heptane and 25 ml $MeCl_2$. To the agitated 2-phase system was added 12.2 gram D(—) phenylglycine butyl ester hydrochloride (0.05 mole) over 20 minutes at 12°-14° C. The layers were allowed to settle.

The lower aqueous layer was re-extracted with 30 ml (2:1) heptane: MeCl$_2$. The two solvent-product layers (upper) were combined and evaporated to 60° C./at 29" vac. The stripped liquid residue=10.3 grams D(−)phenylglycine butyl ester (free base) (Theory=10.4 grams); specific rotation, using sodium lamp D-line wavelength=−85.5° (1 N HCl). IR and NMR spectra confirmed the formation of the free base.

EXAMPLE 8

Synthesis of D(−)phenylglycine isopropylester hydrochloride.

To 200 ml isopropanol was added 59.5 gram D(−)phenylglycine acid chloride hydrochloride (0.24 mole) over 15 minutes with reaction temperature allowed to rise from 25° C. to 55° C., using warming as necessary to maintain temperature at 55° C. Since solution was not complete, 100 ml more isopropanol was added and the reaction temperature increased to 65° C., where solution occurs. Cooled to 25° C. and filtered. Air-dry weight of D(−) phenylglycine isopropylester HCl=33.9 grams, specific rotation, using sodium lamp D-line wavelength=−66.3° (1 N HCl).

The filtrate was evaporated to dryness yielding an additional 18.5 grams of phenylglycine isopropylester HCl. Total weight of D(−)phenylglycine isopropylester HCl=52.8 grams (95% of theory).

EXAMPLE 9

Synthesis of D(−)phenylglycine decyl ester hydrochloride

To 200 ml n-decanol ("Lorol 22", DuPont) was added 42.5 grams D(−)phenylglycine acid chloride hydrochloride (0.206 mole) over 15 minutes, with reaction temperature allowed to rise from 25° to 85° C., using warming as necessary to maintain temperature at 85° C. Clear solution resulted. Cooling to 45° C. gives crystallization. Added 200 ml heptane and cooled to 10° C. Filtered and washed cake with 100 ml hexane. Air-dry weight of white needles=53 grams (78.4% theory) D(−)phenylglycine decyl ester HCl, specific rotation, using sodium lamp D-line wavelength=−50.3° (1 N HCl+MeOH).

EXAMPLE 10

Synthesis of L-(+)-phenylglycine butyl ester hydrochloride via L(+)-phenylglycine Anhydrous HCl (41.3 gram) was bubbled into a mixture of 60 grams L(+)-phenylglycine (0.40 mole) in 360 ml n-butanol, at a temperature of 50°-55° C., over 2½ hours. The reaction mixture thickens, then thins, and then dissolves upon heating to 95° C. for ½ hour.

Evaporated total reaction mixture to dryness at 75° C. bath temperature and 25 mm vacuum. Weight of evaporated and air-dried solids (L-(+)-phenylglycine butyl ester hydrochloride)=93.8 grams; 96.3% yield; specific rotation, using sodium lamp D-line wavelength=(+) 90.8° (1 N HCl). This butyl ester hydrochloride salt was used in Example 11.

EXAMPLE 11

Resolution of racemic mandelic acid with L-(+)-phenylglycine n-butyl ester hydrochloride A mixture of 48.7 grams L-(+)-phenylglycine butyl ester hydrochloride (0.20 mole), 60.8 grams racemic mandelic acid (0.40 mole) and 1300 water was stirred at 25° C. until solution occurred (15 minutes). An insoluble, tan precipitate was filtered off.

To the filtrate was added 6.0 grams NaOH dissolved in 6 grams water gradually at 23°-27° C. After addition of NaOH, the glass walls of the container were scratched with a glass rod to initiate crystallization. A flocculent precipitate formed gradually, becoming too thick to stir well after about 1 hour of stirring.

Filtered thick slurry and washed cake with 200 ml of water (5° C.). Air-dry weight of solids (impure L(+)-phenylglycine butyl ester D(−)-mandelic acid)=72.6 grams, specific rotation, using sodium lamp D-length=+28.1° (1 N HCl).

Dissolved 29.6 grams (0.0825 mole) of impure L(+)-phenylglycine butyl ester D(−)-mandelic acid in 150 ml water containing 8.42 grams 95% H$_2$SO$_4$ (0.0825 gram). The aqueous solution was extracted with methyl isobutyl ketone to remove free D(−)-mandelic acid and the extracts evaporated to dryness. The evaporated residue was dissolved in a solution of 6 grams NaOH in 150 ml water, extracted with methylene chloride, acidified with 14.7 grams 95% H$_2$SO$_4$ and extracted again with methyl isobutyl ketone.

Evaporation of the methyl isobutyl ketone to dryness yielded 16.8 grams of optically impure D(−)-mandelic acid, specific rotation, using sodium lamp D-line wavelength=−27.7° (water); over 99% by acid-base titration. Recrystallization from water leads to D(−)-mandelic acid specific rotation, using sodium lamp D-line wavelength=−154° (water); over 99% by acid base titration; identical in NMR and IR with authentic D(−) mandelic acid.

It will be understood that the specification and examples are illustrative, but not limitative of the present invention and that other embodiments within the spirit and scope of the invention will suggest themselves to those skilled in the art.

What is claimed is:

1. Process for the optical resolution of racemic mandelic acid which process comprises contacting said racemic mandelic acid with a phenylglycine ester or a phenylglycine ester hydrochloride in a reaction medium, and recovering the D(−) mandelic acid and L(+)mandelic acid formed.

2. Process as claimed in claim 1 wherein said phenylglycine ester is a D(−)phenylglycine ester.

3. Process as claimed in claim 1 wherein said phenylglycine ester is an L(+)phenylglycine ester.

4. Process as claimed in claim 2 wherein said phenylglycine ester is D(−)phenylglycine methyl ester.

5. Process as claimed in claim 2 wherein said phenylglycine ester is D(−)phenylglycine isopropyl ester.

6. Process as claimed in claim 2 wherein said phenylglycine ester is D(−)phenylglycine n-butyl ester.

7. Process as claimed in claim 2 wherein said phenylglycine ester is D(−)phenylglycine n-decyl ester.

8. Process as claimed in claim 1 wherein said phenylglycine ester hydrochloride is D(−)phenylglycine alkyl ester hydrochloride.

9. Process as claimed in claim 1 wherein said phenylglycine ester is L(+)-phenylglycine ester hydrochloride.

10. Process as claimed in claim 1 wherein said phenylglycine ester is L(+)-phenylglycine methyl ester.

11. Process as claimed in claim 1 wherein said phenylglycine ester is L(+)-phenylglycine n-butyl ester.

12. Process as claimed in claim 1 wherein said phenylglycine ester is L(+)-phenylglycine isobutyl ester.

13. Process as claimed in claim 1 wherein said phenylglycine ester hydrochloride is L(+)-phenylglycine n-butyl ester hydrochloride.

14. Process as claimed in claim 1 wherein said phenylglycine ester is used in an amount of 0.5 to 1 mole per mole of racemic mandelic acid to be resolved.

15. Process as claimed in claim 1 wherein said phenylglycine ester hydrochloride is used in an amount of 0.5 to 1.2 mole per mole of racemic mandelic acid to be resolved.

16. Process as claimed in claim 15 wherein said hydrochloride is neutralized, after contacting of the phenylglycine ester hydrochloride and racemic mandelic acid, with 0.7 to 1 mole of sodium hydroxide per mole of optically pure phenylglycine ester hydrochloride.

17. Process as claimed in claim 1 wherein said resolution medium is water.

18. Process as claimed in claim 1 wherein said resolution medium is a lower alkanol.

19. Process as claimed in claim 17 wherein said medium is a water/lower alkanol mixture.

20. Process as claimed in claim 1 wherein said resolution is carried out at from 0° C. to 35° C.

21. Process as claimed in claim 20 wherein said resolution is carried out at from 20° C. to 30° C.

22. Process as claimed in claim 1 wherein the D(−) and L(+)-mandelic acid components are isolated by extraction.

23. Process as claimed in claim 1 wherein the phenylglycine ester used is D(−)-phenylglycine ester and is recovered after resolution of the mandelic acid by neutralizing the aqueous layer remaining after extraction of D(−)-mandelic acid with an organic solvent.

24. Process as claimed in claim 1 wherein the phenylglycine ester used is L(+)-phenylglycine ester and is recovered after resolution of the mandelic acid by neutralizing the aqueous layer remaining after extraction of L(+)-mandelic acid with an organic solvent.

25. Process for the optical resolution of racemic mandelic acid which process comprises contacting the racemic mandelic acid with D(−)-phenylglycine butyl ester and recovering the D(−)-mandelic acid and L(+)-mandelic acid formed.

26. Process for the optical resolution of racemic mandelic acid which process comprises contacting the racemic mandelic acid with L(+)-phenylglycine butyl ester and recovering the L(+)-mandelic acid and D(−)-mandelic acid formed.

* * * * *